United States Patent
Predescu et al.

(10) Patent No.: US 10,793,598 B2
(45) Date of Patent: Oct. 6, 2020

(54) GRB-EH$_{ITSN}$ INHIBITORY PEPTIDES (71) Applicant: Rush University Medical Center, Chicago, IL (US)

(72) Inventors: Sanda Predescu, Hinsdale, IL (US); Dan Predescu, Hinsdale, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 15/321,109

(22) PCT Filed: Jun. 19, 2015

(86) PCT No.: PCT/US2015/036643
§ 371 (c)(1),
(2) Date: Dec. 21, 2016

(87) PCT Pub. No.: WO2015/200121
PCT Pub. Date: Dec. 30, 2015

(65) Prior Publication Data
US 2017/0129923 A1    May 11, 2017

Related U.S. Application Data (60) Provisional application No. 62/018,315, filed on Jun. 27, 2014.

(51) Int. Cl.
*C07K 7/06* (2006.01)
*A61K 38/00* (2006.01)

(52) U.S. Cl.
CPC ............... *C07K 7/06* (2013.01); *A61K 38/00* (2013.01); *C07K 2319/00* (2013.01); *C07K 2319/10* (2013.01); *G01N 2800/12* (2013.01)

(58) Field of Classification Search
CPC ............... A61K 38/00; C07K 2319/00; C07K 2319/10; C07K 7/06; G01N 2800/12
See application file for complete search history.

(56) References Cited

U.S. PATENT DOCUMENTS

| 7,928,186 B2 | 4/2011 | Chang |
| 2013/0098357 A1 | 4/2013 | Singh |

OTHER PUBLICATIONS

Chérine Bechara, Sandrine Sagan, Cell-penetrating peptides: 20 years later, where do we stand, FEBS Letters 587 (2013) 1693-1702.*
Tonny de Beer, Molecular mechanism of NPF recognition by EH domains, nature structural biology • vol. 7 No. 11 • Nov. 2000.*
Nicole A. Brooks, Cell-penetrating peptides: Application in vaccine delivery, Biochimica et Biophysica Acta 1805 (2010) 25-34.*
Fortin, T. et al.; "Multiple Reaction Monitoring Cubed for Protein Quantification at the Low Nanogram/Milliliter Level in Nondepleted Human Serum"; Analytical Chemistry, vol. 81; Oct. 2009; pp. 9343-9352.
Extended European Search Report dated Dec. 12, 2017 for European Application No. 15810843.1.
Abe et al.; "Formation of Plexiform Lesions in Experimental Severe Pulmonary Arterial Hypertension"; Circulation, vol. 121, No. 25; Jun. 29, 2010; pp. 2747-2754.
Aliotta et al.; "Induction of pulmonary hypertensive changes by extracellular vesicles from monocrotaline-treated mice"; Cardiovascular Research, vol. 100; Dec. 1, 2013; pp. 354-362.
Altschul et al.; "Gapped BLAST and PSI-BLAST: a new generation of protein database search programs"; Nucleic Acids Research, vol. 25, Issue 17; pp. 3389-3402; Sep. 1, 1997.
Bardita et al.; "In vivo knockdown of intersectin-1s alters endothelial cell phenotype and causes microvascular remodeling in the mouse lungs"; Apopstosis, vol. 18; Jan. 1, 2013; pp. 57-76.
Barnidge et al.; "Identification of transmembrane tryptic peptides of rhodopsin using matrix-assisted laser desorption/ionization time-of-flight mass spectrometry"; Protein Science, vol. 6; Apr. 1, 1997; pp. 816-824.
De Beer et al. "Molecular mechanism of NPF recognition by EH domains"; Nature Structural Biology, vol. 7, No. 11; Nov. 1, 2000; pp. 1018-1022.
George et al.; "Transgenic expression of human matrix metalloproteinase-9 augments monocrotaline-induced pulmonary arterial hypertension in mice"; Journal of Hypertension, vol. 29, No. 2; Feb. 2011; pp. 299-308.
Gurland et al.; "Rapid Events in Growth Hormone Action. Induction of *c-fos* and *c-jun* Transcription in 3T3-F442A Preadipocytes"; Endocrinology, vol. 127, No. 6; Dec. 1, 1990; pp. 3187-3195.
Henikoff et al.; "Amino acid substitution matrices from protein blocks"; Proceedings of the National Academy of Sciences, vol. 89, No. 22; Nov. 1992; pp. 10915-10919.
Jonigk et al.; "Plexiform Lesions in Pulmonary Arterial Hypertension: Composition, Architecture and Microenvironment"; The American Journal of Pathology, vol. 179, No. 1; Jul. 2011; pp. 167-179.
Karlin et al.; "Applications and statistics for multiple high-scoring segments in molecular sequences"; Proceedings of the National Academy of Sciences, vol. 90, No. 12; Jun. 15, 1993; pp. 5873-5877.

(Continued)

*Primary Examiner* — James H Alstrum-Acevedo
*Assistant Examiner* — Erinne R Dabkowski
(74) *Attorney, Agent, or Firm* — Barnes & Thornburg LLP (57) ABSTRACT

Fusion peptides and methods of inhibiting GrB-EHITSN or a fragment thereof are provided. The fusion peptides include an NPF peptide and a cell-permeable peptide operably connected thereto. Fusion peptides and methods of inhibiting activity of GrB-EHITSN or fragment thereof are provided. An aspect includes a fusion peptide comprising an isolated NPF peptide comprising an amino acid sequence having at least 90% identity to SEQ ID NO: 2 and a cell-permeable peptide operably connected to the isolated NPF peptide, wherein the fusion peptide inhibits activity of GrB-EHITSN or a fragment thereof.

8 Claims, 3 Drawing Sheets
Specification includes a Sequence Listing.

(56) References Cited

OTHER PUBLICATIONS

Keiken et al.; "Structural insight into the interaction of proteins containing NPF, DPF, and GPF motifs with the C-terminal EH-domain of EHD1"; Protein Science, vol. 18; Oct. 1, 2009; pp. 2471-2479.
Launay et al.; "Serotonin 5-$HT_{2B}$ receptors are required for bone-marrow contribution to pulmonary arterial hypertension"; Blood, vol. 119, No. 7; Feb. 16, 2012; pp. 1772-1780.
Patel et al.; "A novel p38 mitogen-activated protein kinase/Elk-1-dependent molecular mechanism underlying abnormal endothelial cell proliferation in plexogenic pulmonary arterial hypertension"; Journal of Biological Chemistry, vol. 288, No. 52; Dec. 27, 2013; pp. 1-31.
Patel et al.; "A Novel p38 Mitogen-activated Protein Kinase/Elk-1 Transcription Factor-dependent Molecular Mechanism Underlying Abnormal Endothelial Cell Proliferation in Plexogenic Pulmonary Arterial Hypertension"; The Journal of Biological Chemistry, vol. 288, No. 36; Sep. 6, 2013; pp. 25701-25716.
Qin et al.; "The Polyphenols Resveratrol and S17834 Prevent the Structural and Functional Sequelae of Diet-Induced Metabolic Heart Disease in Mice"; Circulation, vol. 125, Issue 14; Apr. 10, 2012; pp. 1757-1764.
Schatz et al.; "Interaction of the HIV-1 Rev cofactor eukaryotic initiation factor 5A with ribosomal protein L5"; Proceedings of the National Academy of Sciences, vol. 95; Feb. 1, 1998; pp. 1607-1612.
International Search Report completed Sep. 1, 2015 for International Application No. PCT/US2015/036643.
Written Opinion completed Sep. 1, 2015 for International Application No. PCT/US2015/036643.

\* cited by examiner

GRB-EH$_{ITSN}$ INHIBITORY PEPTIDES

RELATED APPLICATIONS

This application claims the benefit under 35 U.S.C. § 371 of International Application No. PCT/US2015/036643, filed Jun. 19, 2015, which claims the benefit of U.S. Provisional Application No. 62/018,315, filed Jun. 27, 2014, which are incorporated by reference herein in their entirety.

SEQUENCE LISTING

The instant application contains a Sequence Listing which has been submitted electronically in ASCII format and is hereby incorporated by reference in its entirety. The ASCII copy, created on Jun. 12, 2015, is named 14904-107 Sequence Listing_ST25.txt and is approximately 6.8 KB in size.

TECHNICAL FIELD

The present invention relates to fusion peptides and methods of inhibiting activity of GrB-EH$_{ITSN}$ or fragments thereof.

BACKGROUND

Human pulmonary arterial hypertension (PAH) is a disease of small pulmonary arteries characterized by vascular proliferation, remodeling and progressive formation of plexiform lesions (PLs) that increase pulmonary vascular resistance, leading ultimately to right ventricular failure and death. A plexiform lesion is the hallmark of sustained and irreversible PAH and is defined as focal disruption of the internal elastic lamina of a muscular pulmonary artery by a "glomeruloid" with focal proliferation of endothelial channels. Formation of PLs resulting in narrowing of the lumen of pulmonary artery is the major factor responsible for the high vascular resistance in severe PAH.

Currently, there is no treatment for plexogenic PAH. Despite a general agreement on the importance of angiogenic proliferation of endothelial cells (ECs) in vascular remodeling in human PAH and the need for therapeutics to target the underlying ECs abnormalities, no strategy has thus far proven effective, suggesting that a critical piece of the mechanism is missing. Thus, current therapies target pulmonary artery smooth muscle cell proliferation or vasodilation and simply delay progression rather than reverse the disease. A need exists for therapeutic peptides and methods of treatment for decreasing EC proliferation. In addition, peptides and methods for reducing the proliferative effect of a protein fragment, GrB-EH$_{ITSN}$, comprising two Epsin15 homology domains (EH) that is a proteolytic cleavage product generated by granzyme B (GrB) cleavage of intersectin-1s (ITSN-1s) (GrB-EH$_{ITSN}$) are needed for single or combination therapies for specifically targeting a disease with multi-factorial etiology.

BRIEF SUMMARY

Fusion peptides and methods of inhibiting activity of GrB-EH$_{ITSN}$ or fragments thereof are provided.

An aspect includes a fusion peptide comprising an isolated NPF peptide comprising an amino acid sequence having at least 90% identity to SEQ ID NO: 2 and a cell-permeable peptide operably connected to the isolated NPF peptide, wherein the fusion peptide inhibits activity of GrB-EH$_{ITSN}$ or a fragment thereof.

Other aspects include isolated nucleic acids encoding the fusion peptides described herein and vectors and host cells.

Methods of inhibiting GrB-EH$_{ITSN}$ or a fragment thereof are provided. The method includes administering a therapeutically effective amount of a fusion peptide comprising an isolated NPF peptide comprising an amino acid sequence having at least 90% identity to SEQ ID NO: 2 and a cell-permeable peptide operably connected to the isolated NPF peptide and inhibiting the activity of GrB-EH$_{ITSN}$ or the fragment thereof.

Advantages of the present invention will become more apparent to those skilled in the art from the following description of the preferred embodiments of the present invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION

The present invention provides fusion peptides and methods of inhibiting activity of GrB-EH$_{ITSN}$ or fragments thereof.

Intersectin-1 protein (ITSN-1s) is a cytoplasmic membrane-associated protein and a cytosolic protein. The membrane associated ITSN-1s indirectly coordinates endocytic membrane traffic with the actin assembly machinery. ITSN-1s is a substrate for the protease GrB. (Patel et al., 2013, JBC).

As used herein, the term "inhibit", "inhibiting", or "inhibit the activity" of the GrB-EH$_{ITSN}$ or fragments thereof refers to slowing, interrupting, arresting or stopping the activity of GrB-EH$_{ITSN}$ or fragments thereof, and does not necessarily indicate a total elimination of the activity. The terms "inhibit" and "inhibiting", or the like, denote quantitative differences between two states, refer to at least statistically significant differences between the two states. For example, "an amount effective to inhibit the activity of GrB-EH$_{ITSN}$ or a fragment thereof" means that activity will be at least statistically significantly different from the untreated cells. Such terms are applied herein to, for example, rates of cell proliferation "Treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to GrB-EH$_{ITSN}$ or a halting in the progression of a disease such as pulmonary arterial hypertension.

The term "subject" or "patient" as used herein, refers to a mammal, preferably a human.

In some embodiments, practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

The terms "protein," "peptide" and "polypeptide" are used interchangeably herein.

The amino acid sequence as used herein may be in the form of a fusion peptide in which an NPF peptide is conjugated to a cell-permeable peptide. The cell-permeable peptides may be attached either on the N- or C-terminus region of the NFP peptide or can be generated as a recombinant conjugate by generating cDNA and cloning using molecular biology tools.

The term "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least about 40%, 50%, 60%, 70%, 80%, 90%, 95%, 96%, 97%, 98%, to 99% sequence identity to the native (endogenous) nucleotide sequence.

The term "conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, 91%, 92%, 93%, 94%, 95%, 96%, 97%, 98% or 99% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence, such as an RNA nucleotide complementary to a DNA nucleotide. Preferably, the substantial identity exists over a region that is at least about 6-7 amino acids or 25 nucleotides in length.

An example of an algorithm that is suitable for determining percent sequence identity and sequence similarity is the BLAST algorithm, which is described in Altschul et al., 1977, Nuc. Acids Res. 25:3389-3402. BLAST is used, with the parameters described herein, to determine percent sequence identity for the nucleic acids and proteins of the invention. Software for performing BLAST analysis is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA,* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Pharmaceutical Compositions

The peptide described herein may be used alone or in compositions together with a pharmaceutically acceptable carrier or excipient. Pharmaceutical compositions of the present invention comprise a therapeutically effective amount of a fusion peptide including an NPF peptide and a membrane permeable peptide formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The fusion peptides described herein may be administered to humans and animals in dosage unit formulations containing conventional nontoxic pharmaceutically acceptable carriers, adjuvants, and vehicles as desired.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules or lipid particles, lyophilized powders, or other forms known in the art.

Compositions of the invention may be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 m. Further, the formulation preferably has balanced osmolarity ionic strength and chloride concentration, and the smallest aerosolizable volume able to deliver effective dose of the peptides of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 µm. Predominantly in this application means that at least 70% but preferably more than 90% of all generated aerosol particles are within 1-5 µm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDESTREAM nebulizers (Medic-Aid Ltd., West Sussex, England), PARI LC and PARI LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

Solid dosage forms for oral administration include capsules, tablets, pills, powders, and granules. In such solid dosage forms, the active peptide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active peptides can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active peptide may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active peptides, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a peptide of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active peptide of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Peptides of the invention may also be formulated for use as topical powders and sprays that can contain, in addition to the peptides of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a peptide to the body. Such dosage forms can be made by dissolving or dispensing the peptide in the proper medium. Absorption enhancers can also be used to increase the flux of the peptide across the skin. The rate can be controlled by either providing a rate controlling membrane or by dispersing the peptide in a polymer matrix or gel. The peptides of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a peptide of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

A fusion peptide described herein can be administered alone or in combination with other peptides, for a possible combination therapy being staggered or given independently of one another. Long-term therapy is equally possible as is adjuvant therapy in the context of other treatment strategies, as described above. Other possible treatments are therapy to maintain the patient's status after the initial treatment, or even preventive therapy, for example in patients at risk.

Effective amounts of the peptide of the invention generally include any amount sufficient to detectably inhibit the activity of GrB-EH$_{ITSN}$ or fragments thereof, or by detecting an inhibition or alleviation of symptoms. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific peptide employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

If the fusion peptide is administered in combination with another compound, the term "amount that is effective to inhibit activity of GrB-EH$_{ITSN}$ or fragments thereof" is understood to mean that amount of a fusion peptide in combination with the additional compound to achieve the desired effect. In other words, a suitable combination therapy according to the current invention encompasses an amount of the peptide and an amount of the additional compound, either of which when given alone at that particular dose would not constitute an effective amount, but administered in combination would be an "amount that is effective inhibit activity of GrB-EH$_{ITSN}$ or fragments thereof".

It will be understood, however, that the total daily usage of the peptides and compositions of the present invention will be decided by the attending physician within the scope of sound medical judgment. The specific therapeutically effective dose level for any particular patient will depend upon a variety of factors including the disorder being treated and the severity of the disorder; the activity of the specific peptide employed; the specific composition employed; the age, body weight, general health, sex and diet of the patient; the time of administration, route of administration, and rate of excretion of the specific peptide employed; the duration of the treatment; drugs used in combination or coincidental with the specific peptide employed; and like factors well known in the medical arts.

The dose of a peptide to be administered to warm-blooded animals, for example humans of approximately 70 kg body weight, is preferably from approximately 3 mg to approximately 5 g, more preferably from approximately 10 mg to approximately 1.5 g, most preferably from about 100 mg to about 1000 mg per person per day, divided preferably into 1 to 3 single doses which may, for example, be of the same size. Usually, children receive half of the adult dose.

Peptide

Intersectin-1s (ITSN-1s), a highly prevalent protein of lung ECs, is a novel identified substrate for the cytotoxic protease GrB, (Patel et al., 2013, JBC) with a conserved cleavage site (IDQD$^{271}$GK) throughout the evolution. Under inflammatory conditions associated with increased GrB levels, such as plexiform PAH, ITSN-1s is cleaved by GrB. The proteolytic cleavage of ITSN-1s generates a protein fragment, GrB-EH$_{ITSN}$, comprising two Epsin15 homology domains (EH), with EH2 better conserved (shown in SEQ ID NO: 1 below). Cultured ECs, animal models of PAH and human PAH biospecimens have been used to show that GrB-EH$_{ITSN}$ possesses EC proliferative potential mediated via a novel p38 MAPK/Elk-1 transcription factor and c-fos immediate early response gene-dependent signaling and that this pathway may be responsible for formation of plexiform lesions in PAH (Patel et al., 2013. JBC).

Amino acids 201-300 of ITSN (SEQ ID NO: 1) are shown below with the EH2 domain in bold (aa 215-293). W263 (underlined) is the conserved residue critical for the interaction with the NPF.

```
                                        (SEQ ID NO: 1)
AQSFDVASVP PVAEWAVPQS SRLKYRQLFN SHDKTMSGHL

TGPQARTILM QSSLPQAQLA SIWNLSDIDQ DGKLTAEEFI

LAMHLIDVAM SGQPLPPVLP
```

The peptide motif NPF is the essential target of EH domains and binding is enhanced when Thr or Ser occupy the two positions preceding NPF and when a hydrophobic or basic residue follows (Salcini, 1997; deBeer, 1998).

In order to inhibit EC proliferation, for example, in response to the presence of GrB-EH$_{ITSN}$, an inhibitory peptide was generated.

The inhibitory peptide includes an NPF motif. In some embodiments, the NPF motif comprises the residues PTGSSSTNPFL (SEQ ID NO: 2) or at least 80% identity, 85% identity, 90% identity, 95% identity to SEQ ID NO: 2. The inhibitory peptide further includes a membrane permeable motif operably connected to the NPF motif. In some embodiments, a penetratin membrane permeable motif is operably connected to the NPF motif. In some embodiments, the inhibitory peptide includes the penetratin membrane permeable motif comprising the residues RQIKIWFQN-RRMKWKK (SEQ ID NO: 3) or at least 80% identity, 85% identity, 90% identity, 95% identity to SEQ ID NO: 3 operably connected to the NPF motif. Other penetrating membrane permeable motifs comprising penetratin may also be included as well as other membrane permeable motifs. By way of non-limiting example, see Table I listing additional membrane permeable motifs that may be operably connected the NPF motif of SEQ ID NO: 2. In some embodiments, the fusion peptide comprises SEQ ID NO: 3 conjugated to the N-terminus of SEQ ID NO: 2 as follows: RQIKIWFQNRRMKWKKPTGSSSTNPFL (SEQ ID NO: 4) or at least 80% identity, 85% identity, 90% identity, 95% identity to SEQ ID NO: 4.

TABLE I

| Name | Sequence | SEQ ID NO |
|---|---|---|
| 105Y | SIPPEVKFNKPFVYLI | 5 |
| Antennapedia Leader Peptide | KKWKMRRNQFWVKVQRG | 6 |
| Anti Beta Gamma | AAVALLPAVLLALLAVT DQLGEDFFAVDLEAFLQ EFGLLPEKE | 7 |

TABLE I-continued

| Name | Sequence | SEQ ID NO |
|---|---|---|
| Arg9 | RRRRRRRRR | 8 |
| HIV Tat 47 | YGRKKRRQRRR | 9 |
| Lipid Membrane translocating | KKAAAVLLPVLLAAP | 10 |
| MEK1 Nterm | MPKKKPTPIQLNP | 11 |
| MPS | AAVALLPAVLLALLAK | 12 |
| Penetratin | RQIKIWFQNRRMKWKK | 3 |
| Penetratin Arg | RQIRIWFQNRRMRWRR | 13 |
| Penetratin Arg Cys | RQIRIWFQNRRMRWRRC | 14 |
| Penetratin Cys | RQIKIWFQNRRMKWKKC | 15 |
| Pep-1 | KETWWETWWTEWSQPKK KRKV | 16 |
| Transportan | GWTLNSAGYLLGKINLK ALAALAKKIL | 17 |

In some embodiments, the inhibitory peptide may include a marker or tag to facilitate visualization or purification of the peptide. By way of non-limiting example, the inhibitory peptide may include a FITC-tag, Strep-tag, His-tag, Myc-tag and Flag-tag.

EXAMPLES

Example 1

Figure 1:
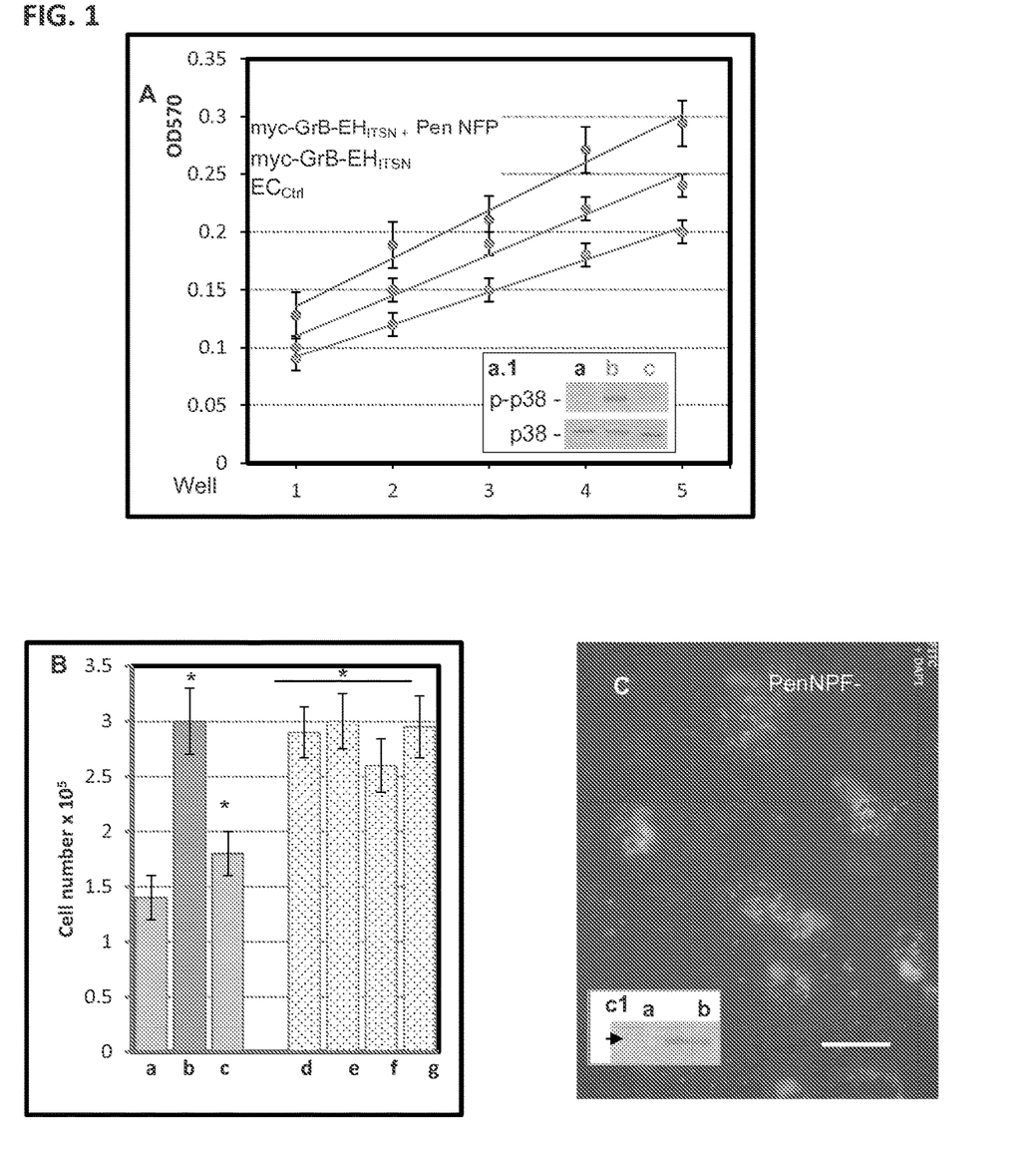
FIGS. 1A-1C illustrate the effect of the GrB-EH$_{ITSN}$ inhibitory peptide on ECs. A. MTT assay applied on EC$_{Ctrl}$, myc-GrB-EH$_{ITSN}$-transfected ECs and myc-GrB-EH$_{ITSN}$-transfected ECs exposed to 12.5 μM PenNFP-FITC peptide for 1 h, 37° C.; p<0.05; WB of cell lysates (inset a1) of EC$_{Ctrl}$ (a), myc-GrB-EH$_{ITSN}$-ECs (b) and myc-GrB-EH$_{ITSN}$-ECs+12.5 μM PenNPF for 1 h, 37° C. (c), using phospho (p)-p38 and p38 Abs. B. Quantification of EC proliferation: EC$_{Ctrl}$ (a), myc-GrB-EH$_{ITSN}$-ECs (b), myc-GrB-EH$_{ITSN}$-ECs+12.5 μM PenNPF (c), myc-GrB-EH$_{ITSN}$-ECs+12.5 μM Pen-AAA (d), myc-GrB-EH$_{ITSN}$-ECs+12.5 μM Pen (e), myc-GrB-EH$_{ITSN}$-ECs+12.5 μM NPF (f), and myc-GrB-EH$_{ITSN}$-ECs+12.5 μM scrambled penNPF, (g). Data in A and B are mean±SEM of 3 independent experiments performed in triplicates. *p<0.05 vs. EC$_{Ctrl}$. C. Fluorescence microscopy of ECs exposed to 12.5 μM PenNPF-FITC, fixed and mounted on glass slides with Prolong Antifade with DAPI. Bar: 50 μm. Inset c1. EC$_{Ctrl}$ (a) and myc-GrB-EH$_{ITSN}$-ECs (b) lysates resolved on SDS PAGE and transferred to nitrocellulose membranes were overlaid with the PenNFP-FITC. FITC Ab detected a direct interaction myc-GrB-EH$_{ITSN}$/PenNFP-FITC; n=3.

ECs stably transfected with the myc-GrB-EH$_{ITSN}$ [selected based on neomycin-resistance], were treated with the PenNPF-FITC peptide to address whether inhibition of GrB-EH$_{ITSN}$ ameliorates EC proliferation. MTT [[3-(4,5-dimethyl thiazol-2-yl)-2,5-diphenyl tetrazolium bromide], assay (Patel et al., 2013. JBC) indicated that exposure of myc-GrB-EH$_{ITSN}$ transfected cells to the PenNPF-FITC peptide inhibits cell growth compared to transfected ECs not exposed to the PenNPF-FITC peptide, FIG. 1A. The OD$^{570}$ values in all the wells containing myc-GrB-EH$_{ITSN}$-transfected cells exposed to the PenNPF-FITC peptide were close to the OD$^{570}$ values of control ECs. A growth curve was generated to relate the OD$^{570}$ values to the cell number per well. The extent of cell growth calculated on 3 successive points on the curve indicated greater than 35% decrease in the number of myc-GrB-EH$_{ITSN}$-transfected cells exposed to the PenNPF-FITC peptide compared to transfected ECs not exposed to the PenNPF-FITC peptide, Quantification of EC proliferation is shown in FIG. 1B as follows: EC$_{Ctrl}$ (a), myc-GrB-EH$_{ITSN}$-ECs (b), myc-GrB-EH$_{ITSN}$-ECs+12.5 µM PenNPF (c), myc-GrB-EH$_{ITSN}$-ECs+12.5 µM Pen-AAA (d), myc-GrB-EH$_{ITSN}$-ECs+12.5 µM Pen (e), myc-GrB-EH$_{ITSN}$-ECs+12.5 µM NPF (f), and myc-GrB-EH$_{ITSN}$-ECs+12.5 µM scrambled penNPF [PTNGSPSSFTL (SEQ ID NO: 22)], (g). Fluorescent imaging of ECs exposed to the PenNPF-FITC peptide indicates efficient internalization, FIG. 1C. Remarkably, exposure of GrB-EH$_{ITSN}$-transfected ECs to the PenNPF-FITC peptide, for 24 h, also caused phospho-p38 inhibition, FIG. 1A inset, (c vs. b). Inset c1. EC$_{Ctrl}$ (a) and myc-GrB-EH$_{ITSN}$-ECs (b) lysates resolved on SDS PAGE and transferred to nitrocellulose membranes were overlaid with the PenNFP-FITC. FITC Ab detected a direct interaction myc-GrB-EH$_{ITSN}$/PenNFP-FITC; n=3. Data shown in FIG. 1 indicate that the GrB-EH$_{ITSN}$ inhibitory peptide (PenNPF) decreases the ECs proliferative potential of GrB-EH$_{ITSN}$ and p38 activation.

Example 2

GrB-EH$_{ITSN}$ has EC proliferative potential in vivo. To address the proliferative potential of GrB-EH$_{ITSN}$ in vivo, the myc-GrB-EH$_{ITSN}$ DNA plasmid was delivered via cationic liposomes into mouse lungs. (Knezevic, 2011). WB using myc Ab applied on lung lysates indicated that the encoded protein is efficiently expressed at 48 h post-delivery, and its lifetime is about 72 h. For continuous and efficient long-term expression of myc-GrB-EH$_{ITSN}$, mice were injected repeatedly every 48 h, for 9 days (Bardita, 2013). Actin was used as loading control. In parallel studies, myc-GrB-EH$_{ITSN}$-transduced mice (FIG. 2B) and wt-controls (FIG. 2A) were subjected to BrdU cell proliferation and morphometric analyses, at day 6 of GrB-EH$_{ITSN}$ treatment (Bardita, 2013). BrdU was injected intra-peritoneally every 24 h, for 2 consecutive days (day 4 and 5 of myc-GrB-EH$_{ITSN}$ treatment). Incorporated BrdU was detected via BrdU-FITC Ab; CD31 Ab/AlexaFluor 594 was used for positive identification of ECs. For morphological assessment of peptide internalization mice were sacrificed 1 h after injection. BrdU incorporation into newly synthesized DNA indicated that myc-GrB-EH$_{ITSN}$ caused more than 1.6-fold increase in BrdU+ ECs relative to controls. Of note, not only ECs (arrowheads) but also other resident cells of the lung displayed increased BrdU incorporation (FIG. 2B, arrows). Transfection with the empty liposomes or empty pReceiver M43-myc vector did not affect the number of BrdU+ ECs by reference to controls (not shown). Data in FIG. 2A-B indicate that the GrB-EH$_{ITSN}$ has EC proliferative in vivo.

Example 3

Figure 3:
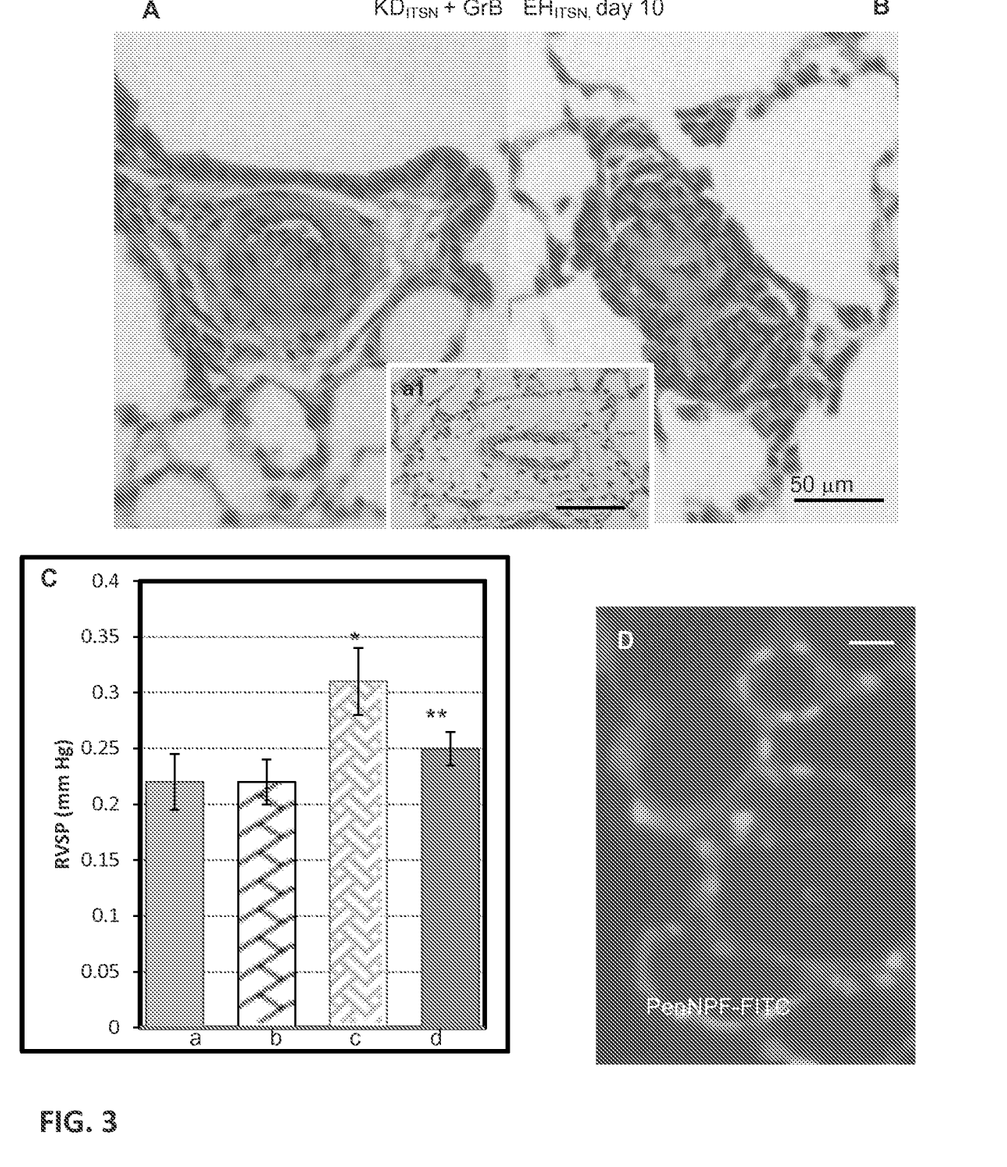
FIGS. 3A-3D illustrate representative H&E staining of lung sections of myc-GrB-EH$_{ITSN}$-KD$_{ITSN}$ mice (A, a1, B) and RVSP measurements (C) in wt-(bar a), empty-Lipo (bar b) and myc-GrB-EH$_{ITSN}$-mice (bar c), 10 days of GrB-EH$_{ITSN}$ treatment. Exposure of myc-GrB-EH$_{ITSN}$-mice to 50 μg PenNPF/mouse caused 20% decrease in RVSP (C, bar d); *p<0.05, **p<0.01. Data are mean±SEM. For morphological assessment of peptide internalization (panel D), mice were sacrificed 1 h after injection. Bars: 50 μm (A, B); 20 μm (a1, D). n=3.

GrB-EH$_{ITSN}$ increases pulmonary pressure in mouse lungs. RVSP measured by right heart catheterization as in (Launay, 2012), at day 10-post initial GrB-EH$_{ITSN}$ delivery showed a 1.36-fold increase in the RVSP in GrB-EH$_{ITSN}$-mice compared to wt- and empty liposomes-treated mice, FIG. 3. The Fulton's index (RV/left ventricle plus septum), indicative of RV hypertrophy, assessed as in (Qin, 2012) was higher in GrB-EH$_{ITSN}$-mice compared to wt-mice (0.31±0.03 vs. 0.22±0.01; means±SEM; p<0.05).

Data in FIG. 3 indicate that the GrB-EH$_{ITSN}$-treated mice display increased pulmonary pressure and hypertrophic RVs, consistent with a PAH phenotype. Treatment of the GrB-EH$_{ITSN}$-treated mice with the PenNPF caused a 20% decrease in RVSP.

Example 4

Figure 2:
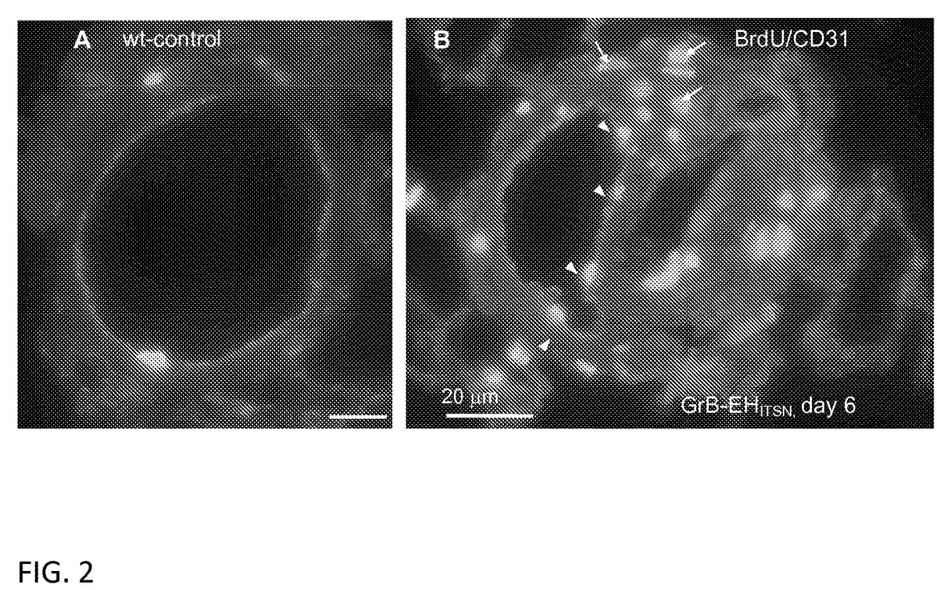
FIGS. 2A-2B illustrate the proliferative effect of the GrB-EH$_{ITSN}$ fragment on EC in vivo. Wt-mice (B) and myc-GrB-EH$_{ITSN}$-treated mice, day 5 of treatment (A) were subjected to BrdU proliferation assay. Data are mean±SEM. All data are representative of 3 mice in each group. Bars: 20 μm.

Identify and quantify GrB/ITSN cleavage products in hPAH lung explants with PLs. Lysates of hPAH lung tissue with prominent PLs and non-disease controls (pulmonary arteries from tissue of donors) will be analyzed by WB as in FIG. 2 for ITSN-1s expression. Representative blots will be subjected to densitometry and results will be expressed as % of ITSN-1s from total ITSN-1s in controls. IHC for GrB, CD8$^{+}$ and the EC specific marker CD31 will be applied on paraffin-embedded hPAH sections as in (Patel, 2013). We will examine PLs and the adjacent arteries with varying degrees of concentric intimal proliferation.

MS studies. PLs, assumed to be enriched in GrB/ITSN fragments, as well as control tissue, sampled from at least 3 locations, will be collected from hPAH lung explants with prominent PLs and non-disease controls. Serial sections of tissue will be used for laser-assisted microdissection as in (Jonigk, 2011). MS studies will be performed using Proteomics/Bio-markers Core and the MS Laboratory of Rush University. The approach relies upon a secondary in vitro proteolytic release of the endogenous substrates with chymotrypsin to provide secondary peptides from the larger proteolytic fragments, as in (Barnidge, 2003; Fortin, 2009; Gurland, 1990). The fragments generated will fall into 3 groups (Table 2): uncleaved substrate, the GrB-EH$_{ITSN}$, and the GrB-SH3A-E$_{ITSN}$. Isotopically-labeled, synthetic internal standard peptides for each of the target peptide will be spiked (5 pg/mL) into each specimen (tissue homogenates) immediately prior to processing. All specimens will then be digested with chymotrypsin, using manufacturer protocols, fractionated (10 kDa Amicon Ultrafree-MC spin filter) to partially-resolve target peptides from larger fragments, and then loaded onto an Agilent 43 mm 300 Å C18 chip with 40 nL trapping column. The column will be washed, eluted (linear gradient of acetonitrile containing 1% formic acid) and analyzed on an Agilent 6410 triple quad MS equipped with an Agilent 1200 series Chip-cube HPLC using multiple reaction monitoring (MRM)-triggered MS/MS experiments (target masses listed below). A standard curve (0.1 pg/mL-1 µg/mL) and quality control samples (5 and 500 pg/mL) of the internal standards will then be performed for all target peptides. A linear or quadratic regression method will be produced from this run and used to quantify the levels of each targeted cytokine and peptide. From these data, the test performance characteristics (assay range, LOQ, LOD, % CV, etc.) will be calculated for each target. Then, a Shimadzu QIT MS will also be used to evaluate efficiency of all enzymatic digestions and characterize the resulting digested peptides for unexpected cleavage products.

TABLE 2

| Digestion | Digestion* | Peptide Fragment | sequence | Mass | Mass (internal) |
|---|---|---|---|---|---|
| GrB | Chemotrypsin | | | | |
| - | + | Uncleaved | NLSDIDQDGKLTAEEF (SEQ ID NO: 18) | 1794.8392 | 1816.8392 |
| + | + | GrB-EH$_{ITSN}$ | NLSDIDQD (SEQ ID NO: 19) | 919.4003 | 931.4003 |
| + | + | GrB-SH3A-E$_{ITSN}$ | GKLTAEEF (SEQ ID NO: 20) | 894.4567 | 904.4567 |

*Fragments not digested by chymotrypsin will only be observed with the Shimadzu QIT. The sequence NLSDIDQDQGKLTAEEFILA (SEQ ID NO: 21) will also be synthesized to serve as the chymotrypsin digestion control. Please note, the bold/underlined residues represent positions where isotopically labeled (13C) residues will be incorporated to serve as internal standard peptides. Labeled control peptides will be prepared by the MS Core of the RRC at UIC.

Example 5

GrB-EH$_{ITSN}$ elicits a mouse pulmonary EC proliferative response and vascular remodeling that can be ameliorated via a GrB-EH$_{ITSN}$ inhibitory peptide.

The objective is to assess the proliferative response and PAH development in GrB-EH$_{ITSN}$-transduced KD$_{ITSN}$ mice and to test the possibility of amelioration the effects of GrB-EH$_{ITSN}$ via a GrB-EH$_{ITSN}$ inhibitory peptide. The working hypothesis is that GrB-EH$_{ITSN}$ is the "trigger" of the plexogenic EC phenotype which is central to PLs formation and that intervention against the GrB-EH$_{ITSN}$ ameliorates EC proliferation and improves PAH in mice. Experiments will use GrB-EH$_{ITSN}$-transduced KD$_{ITSN}$ mice, a range of biochemical/morphological methods (WB, Immunohistochemistry, BrdU assay) and measurements of RVSP/RV hypertrophy. GrB-EH$_{ITSN}$ inhibitory peptide will be delivered to mice to test whether the GrB-EH$_{ITSN}$ inhibitory peptide can attenuate EC proliferation and lung vascular remodeling.

Delivery of GrB-EH$_{ITSN}$ inhibitory, Pen peptides to mice. Myc- and FITC-Pen-NPF as well as control peptides will be solubilized in sterile PBS and injected retro-orbitally, following 2 protocols:

Prevention protocol: the myc-GrB-EH$_{ITSN}$/lipoplexes will be injected with concomitant Pen peptides treatment; Improving protocol: Pen peptides will be injected for 5 consecutive days, day 10 to 14 post first myc-GrB-EH$_{ITSN}$/lipoplexes treatment with continuous myc-GrB-EH$_{ITSN}$ treatment in day 10 and day 12. Mice will be sacrificed in day 15 post first myc-GrB-EH$_{ITSN}$ injection. Mice with no Pen peptide treatment will serve as controls. At the end of the treatment, the lungs will be assessed for PAH pathology as described below. Peptide internalization by lung endothelium will be studied morphologically (FITC-tag, fluorescent imaging) on paraffin-embedded tissue sections; peptide uptake and the interactions with myc-Gr-BEH$_{ITSN}$ will be investigated in lung lysates by WB, at several time points during experimental procedure.

Histology and immunohistochemistry will be applied on paraffin-embedded lung tissue sections of control and GrB-EH$_{ITSN}$-treated KD$_{ITSN}$ mice as in (Bardita, 2013). Routine histo-pathological examination will be performed by Hematoxylin & Eosin staining. Incorporated BrdU and EC identity will be evaluated by double BrdU/CD31 immunohistochemistry on BrdU reagent injected mice. Lack of smooth muscle actin immunoreactivity will confirm the EC phenotype. Controls for specific staining will be carried out by omitting the primary Abs. Data will be expressed as total number of BrdU$^+$ cells/per 50 small pulmonary vessels (10-100 µm diameter). EC proliferation and apoptosis-resistance will be assessed by immunohistochemistry and WB for several EC proliferation markers (VEGFR-2, HIF-1α and HIF1β), and anti-apoptotic factors (Bcl-X$_L$, survivin, phospho-Bad). For image analysis, slides will be examined using a Zeiss AxioImager microscope, digital camera and Zeiss imaging software.

RVSP/RV hypertrophy will be evaluated by right heart catheterization. Briefly, a 26-gauge needle connected to a pressure transducer will be gently inserted into the heart RV. Pressure wave forms will be monitored in real-time in the continuous sampling acquisition mode and recorded for at least 10 min/mouse. Then, the heart will be removed and the RV will be dissected from the left ventricle and septum and the weight ratio will provide the Fulton's index values. To compare and integrate the morphological and functional features of this new GrB-EH$_{ITSN}$-transduced KD$_{ITSN}$ mouse model of PAH with established and better characterized PAH models, we will use the SU5416/Hx rat for histopathology (Abe, 2010) and the MCT-induced PAH mouse that displays pulmonary inflammation, hypertrophy of PAs with occlusion of precapillary vessels and 2.5-fold elevation in RVSP (George, 2011; Aliotta, 2013; Patel, 2013) for hemodynamics.

Example 6

Investigate the effects of GrB-EH$_{ITSN}$ inhibitory, Pen peptides on p38/Elk-1/c-fos signaling. The Pen-NPF peptide is supposed to ameliorate EC proliferation via inhibition of GrB-EH$_{ITSN}$-mediated p38/Elk-1/c-fos signaling. Lung tissue collected for biochemical investigation in Sub aims 3a and 3b will be also used to determine p38 phosphorylation, p38-Erk1/2 ratio activity, Elk-1 TCF and c-fos IER gene activation. We expect to show that intervention against GrB-EH$_{ITSN}$ ameliorates EC proliferation and causes improvement in myc-GrB-EH$_{ITSN}$-transduced KD$_{ITSN}$ mice by inhibition of p38/Elk-1/c-fos signaling. While cell permeable peptides do not have cell specificity and spread all around the body, they will not affect the EH domains of ITSN in other cells, since the EH domains in control conditions are under the inhibitory effect of SH3A-E$_{ITSN}$. An alternative to delivery of siRNA$_{ITSN}$ and myc-GrB-EH$_{ITSN}$, or if longer GrB-EH$_{ITSN}$ treatment will be needed, the KD$_{ITSN}$ mice will be replaced with the heterozygous KO$_{ITSN}$ that similar to PAH animal models, display about 50% reduction in ITSN protein levels.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A method of inhibiting activity of GrB-EH$_{ITSN}$, the method comprising administering a therapeutically effective amount of a fusion peptide comprising an isolated NPF peptide comprising the amino acid sequence of SEQ ID NO: 2 and a cell-permeable peptide operably connected to the isolated NPF peptide and inhibiting the activity of GrB-EH$_{ITSN}$, wherein the therapeutically effective amount of the fusion peptide is delivered to the lung.

2. A method of inhibiting activity of GrB-EHusN, the method comprising administering a therapeutically effective amount of a fusion peptide to a subject in need thereof, the fusion peptide comprising an isolated NPF peptide, wherein the isolated NPF peptide consists of SEQ ID NO: 2, and a cell-permeable peptide operably connected to the isolated NPF peptide.

3. The method according to claim 2, comprising decreasing proliferation of endothelial cells exposed to GrB-EHITSN relative to control endothelial cells.

4. The method according to claim 2, comprising inhibiting p38 activation.

5. The method according to claim 2, wherein the therapeutically effective amount of the fusion peptide treats one or more symptoms of pulmonary arterial hypertension.

6. The method according to claim 2, wherein the therapeutically effective amount of the fusion peptide decreases pulmonary pressure in subjects having pulmonary arterial hypertension.

7. The method according to claim 2, wherein the cell-permeable peptide is SEQ ID NO: 3.

8. A method of inhibiting activity of GrB-EH$_{ITSN}$, the method comprising administering a therapeutically effective amount of a fusion peptide comprising an isolated NPF peptide and a cell-permeable peptide operably connected to the isolated NPF peptide and inhibiting the activity of GrB-EH$_{ITSN}$, wherein the fusion peptide comprises the amino acid sequence of SEQ ID NO: 4.

* * * * *

SEQUENCE LISTING

```
<160> NUMBER OF SEQ ID NOS: 22

<210> SEQ ID NO 1
<211> LENGTH: 100
<212> TYPE: PRT
<213> ORGANISM: Artificial Sequence
<220> FEATURE:
<223> OTHER INFORMATION: Intersectin-1 fragment 201-300

<400> SEQUENCE: 1

Ala Gln Ser Phe Asp Val Ala Ser Val Pro Pro Val Ala Glu Trp Ala
1               5                   10                  15

Val Pro Gln Ser Ser Arg Leu Lys Tyr Arg Gln Leu Phe Asn Ser His
            20                  25                  30

Asp Lys Thr Met Ser Gly His Leu Thr Gly Pro Gln Ala Arg Thr Ile
        35                  40                  45

Leu Met Gln Ser Ser Leu Pro Gln Ala Gln Leu Ala Ser Ile Trp Asn
    50                  55                  60

Leu Ser Asp Ile Asp Gln Asp Gly Lys Leu Thr Ala Glu Glu Phe Ile
65                  70                  75                  80

Leu Ala Met His Leu Ile Asp Val Ala Met Ser Gly Gln Pro Leu Pro
                85                  90                  95

Pro Val Leu Pro
            100

<210> SEQ ID NO 2
<211> LENGTH: 11
<212> TYPE: PRT
<213> ORGANISM: Artificial Sequence
<220> FEATURE:
<223> OTHER INFORMATION: NPF motif

<400> SEQUENCE: 2

Pro Thr Gly Ser Ser Ser Thr Asn Pro Phe Leu
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Penetratin membrane permeable motif

<400> SEQUENCE: 3
```

```
Arg Gln Ile Lys Ile Trp Phe Gln Asn Arg Arg Met Lys Trp Lys Lys
1               5                   10                  15

<210> SEQ ID NO 4
<211> LENGTH: 27
<212> TYPE: PRT
<213> ORGANISM: Artificial Sequence
<220> FEATURE:
<223> OTHER INFORMATION: PenNPF fusion peptide

<400> SEQUENCE: 4

Arg Gln Ile Lys Ile Trp Phe Gln Asn Arg Arg Met Lys Trp Lys Lys
1               5                   10                  15

Pro Thr Gly Ser Ser Thr Asn Pro Phe Leu
            20                  25

<210> SEQ ID NO 5
<211> LENGTH: 16
<212> TYPE: PRT
<213> ORGANISM: Artificial Sequence
<220> FEATURE:
<223> OTHER INFORMATION: 105Y membrane permeable motif

<400> SEQUENCE: 5

Ser Ile Pro Pro Glu Val Lys Phe Asn Lys Pro Phe Val Tyr Leu Ile
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: Antennapedia leader peptide membrane permeable
      motif

<400> SEQUENCE: 6

Lys Lys Trp Lys Met Arg Arg Asn Gln Phe Trp Val Lys Val Gln Arg
1               5                   10                  15

Gly

<210> SEQ ID NO 7
<211> LENGTH: 43
<212> TYPE: PRT
<213> ORGANISM: Artificial Sequence
<220> FEATURE:
<223> OTHER INFORMATION: Anti Beta Gamma membrane permable motif

<400> SEQUENCE: 7

Ala Ala Val Ala Leu Leu Pro Ala Val Leu Leu Ala Leu Leu Ala Val
1               5                   10                  15

Thr Asp Gln Leu Gly Glu Asp Phe Phe Ala Val Asp Leu Glu Ala Phe
            20                  25                  30

Leu Gln Glu Phe Gly Leu Leu Pro Glu Lys Glu
        35                  40

<210> SEQ ID NO 8
<211> LENGTH: 9
<212> TYPE: PRT
<213> ORGANISM: Artificial Sequence
<220> FEATURE:
<223> OTHER INFORMATION: Arg9 membrane permeable motif

<400> SEQUENCE: 8

Arg Arg Arg Arg Arg Arg Arg Arg Arg
1               5
```

```
<210> SEQ ID NO 9
<211> LENGTH: 11
<212> TYPE: PRT
<213> ORGANISM: Artificial Sequence
<220> FEATURE:
<223> OTHER INFORMATION: HIV Tat 47 membrane permeable motif

<400> SEQUENCE: 9

Tyr Gly Arg Lys Lys Arg Arg Gln Arg Arg Arg
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Lipid Membrane translocating membrane permable
      motif

<400> SEQUENCE: 10

Lys Lys Ala Ala Ala Val Leu Leu Pro Val Leu Leu Ala Ala Pro
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: MEK1 Nterm membrane permeable motif

<400> SEQUENCE: 11

Met Pro Lys Lys Lys Pro Thr Pro Ile Gln Leu Asn Pro
1               5                   10

<210> SEQ ID NO 12
<211> LENGTH: 16
<212> TYPE: PRT
<213> ORGANISM: Artificial Sequence
<220> FEATURE:
<223> OTHER INFORMATION: MPS membrane permeable motif

<400> SEQUENCE: 12

Ala Ala Val Ala Leu Leu Pro Ala Val Leu Leu Ala Leu Leu Ala Lys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Penetratin Arg membrane permeable motif

<400> SEQUENCE: 13

Arg Gln Ile Arg Ile Trp Phe Gln Asn Arg Arg Met Arg Trp Arg Arg
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Penetratin Arg Cys membrane permeable motif

<400> SEQUENCE: 14

Arg Gln Ile Arg Ile Trp Phe Gln Asn Arg Arg Met Arg Trp Arg Arg
1               5                   10                  15
```

```
<210> SEQ ID NO 15
<211> LENGTH: 17
<212> TYPE: PRT
<213> ORGANISM: Artificial Sequence
<220> FEATURE:
<223> OTHER INFORMATION: Penetratin Cys membrane permeable motif

<400> SEQUENCE: 15

Arg Gln Ile Lys Ile Trp Phe Gln Asn Arg Arg Met Lys Trp Lys Lys
1               5                   10                  15

Cys

<210> SEQ ID NO 16
<211> LENGTH: 21
<212> TYPE: PRT
<213> ORGANISM: Artificial Sequence
<220> FEATURE:
<223> OTHER INFORMATION: Pep1 membrane permeable motif

<400> SEQUENCE: 16

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 17
<211> LENGTH: 27
<212> TYPE: PRT
<213> ORGANISM: Artificial Sequence
<220> FEATURE:
<223> OTHER INFORMATION: Transportan membrane permeable motif

<400> SEQUENCE: 17

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 18
<211> LENGTH: 16
<212> TYPE: PRT
<213> ORGANISM: Artificial Sequence
<220> FEATURE:
<223> OTHER INFORMATION: artificial peptide

<400> SEQUENCE: 18

Asn Leu Ser Asp Ile Asp Gln Asp Gly Lys Leu Thr Ala Glu Glu Phe
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: artificial peptide

<400> SEQUENCE: 19

Asn Leu Ser Asp Ile Asp Gln Asp
1               5

<210> SEQ ID NO 20
<211> LENGTH: 8
```

```
<212> TYPE: PRT
<213> ORGANISM: Artificial Sequence
<220> FEATURE:
<223> OTHER INFORMATION: artificial peptide

<400> SEQUENCE: 20

Gly Lys Leu Thr Ala Glu Glu Phe
1               5

<210> SEQ ID NO 21
<211> LENGTH: 20
<212> TYPE: PRT
<213> ORGANISM: Artificial Sequence
<220> FEATURE:
<223> OTHER INFORMATION: artificial peptide

<400> SEQUENCE: 21

Asn Leu Ser Asp Ile Asp Gln Asp Gln Gly Lys Leu Thr Ala Glu Glu
1               5                   10                  15

Phe Ile Leu Ala
            20

<210> SEQ ID NO 22
<211> LENGTH: 11
<212> TYPE: PRT
<213> ORGANISM: Artificial Sequence
<220> FEATURE:
<223> OTHER INFORMATION: artificial peptide

<400> SEQUENCE: 22

Pro Thr Asn Gly Ser Pro Ser Ser Phe Thr Leu
1               5                   10
```